United States Patent [19]

Hutmacher et al.

[11] Patent Number: 4,731,445
[45] Date of Patent: Mar. 15, 1988

[54] PREPARATION OF EPSILON-CAPROLACTAM

[75] Inventors: Hans-Martin Hutmacher, Ludwigshafen; Franz Merger, Frankenthal; Franz J. Broecker, Ludwigshafen; Rolf Fischer, Heidelberg; Uwe Vagt, Speyer; Wolfgang Harder, Weinheim; Claus-Ulrich Priester, Meckenheim, all of Fed. Rep. of Germany

[73] Assignee: BASF Aktiengesellschaft, Ludwigshafen, Fed. Rep. of Germany

[21] Appl. No.: 7,585

[22] Filed: Jan. 28, 1987

[30] Foreign Application Priority Data

Jan. 28, 1986 [DE] Fed. Rep. of Germany ....... 3602375

[51] Int. Cl.$^4$ ........................................... C07D 201/08
[52] U.S. Cl. .................................................... 540/538
[58] Field of Search ......................................... 540/538

[56] References Cited

FOREIGN PATENT DOCUMENTS 43-29148 12/1968 Japan ................................... 540/538
1132776 11/1968 United Kingdom .
1191539  5/1970 United Kingdom .

Primary Examiner—Robert T. Bond
Attorney, Agent, or Firm—Keil & Weinkauf

[57] ABSTRACT

Caprolactam is prepared by a process in which
(a) the 5-formylvalerate is reacted with excess ammonia and hydrogen in the presence of an alkanol as the solvent and in the presence of a hydrogenation catalyst under superatmospheric pressure in the liquid phase at from 40° to 130° C.,
(b) excess ammonia and hydrogen are separated off from the reaction mixture,
(c) the resulting reaction mixture is reacted with water at elevated temperatures with simultaneous removal of alkanols, and
(d) the reaction mixture thus obtained is heated to 150°–370° C. and $\epsilon$-caprolactam is obtained.

10 Claims, No Drawings

PREPARATION OF EPSILON-CAPROLACTAM

The present invention relates to a process for the preparation of ε-caprolactam from 5-formylvalerates.

British Patent No. 1,191,539 describes a process for the preparation of ε-caprolactam in which the 5-formylvalerate is reacted with hydrogen, ammonia and steam in the gas phase at 260° C. in the presence of a copper catalyst. However, difficulties are encountered in the form of the poor vaporizability of the thermally labile 5-formylvalerate and the inadequate catalyst life. Japanese Patent Publication No. 29148/1968 furthermore discloses that 5-formylvalerates can be reacted with ammonia in the presence of water at 230° C. and under 150 bar, and in the presence of Raney nickel in the liquid phase. This process has the disadvantage that the yields fluctuate very greatly when the process is carried out industrially.

It is an object of the present invention to provide a process for the preparation of ε-caprolactam starting from a 5-formylvalerate, the said process giving high yields and a very small amount of by-product.

We have found that this object is achieved by a process for the preparation of ε-caprolactam by reacting a 5-formylvalerate with excess ammonia and with hydrogen in the presence of a hydrogenation catalyst and of a solvent at elevated temperatures under superatmospheric pressure in the liquid phase, wherein
(a) the 5-formylvalerate is reacted with excess ammonia and hydrogen in the presence of an alkanol as the solvent and in the presence of a hydrogenation catalyst under superatmospheric pressure in the liquid phase at from 40° to 130° C.,
(b) excess ammonia and hydrogen are separated off from the reaction mixture,
(c) the resulting reaction mixture is reacted with water at elevated temperatures with simultaneous removal of alkanols, and
(d) the reaction mixture thus obtained is heated to 150°–370° C. and ε-caprolactam is obtained.

The novel process has the advantage that it gives high yields and a small amount of by-products.

Preferred 5-formylvalerates are alkyl 5-formylvalerates, in particular those of $C_1$–$C_4$-alkanols, such as methyl, ethyl, propyl, isopropyl or n-butyl esters. Accordingly, suitable starting compounds are methyl 5-formylvalerate, propyl 5-formylvalerate, isopropyl 5-formylvalerate, ethyl 5-formylvalerate and n-butyl 5-formylvalerate. Methyl 5-formylvalerate has become particularly important industrially.

The reaction in stage a) is carried out in the presence of an alkanol as the solvent. Alkanols corresponding to the alcohol component of the 5-formylvalerate are advantageously used. Accordingly, preferred solvents are methanol, ethanol, propanol, isopropanol and n-butanol. The combination methyl 5-formylvalerate/methanol is particularly preferred. Advantageously, the 5-formylvalerates are used in the form of a 1–50, preferably 2–35, in particularly 5–25, % strength by weight solution in one of the stated solvents.

Ammonia is used in excess in the reaction. Advantageously, from 2 to 50 moles of ammonia are used per mole of 5-formylvalerate. Particularly good results are obtained if from 5 to 30, in particular from 10 to 25, moles of ammonia are used per mole of 5-formylvalerate.

The reaction is carried out in the liquid phase at from 40° to 130° C., advantageously from 40° to 95° C., in particular from 60° to 90° C.

From 1 to 20 moles of hydrogen are advantageously used per mole of 5-formylvalerate. It has proven advantageous to maintain a hydrogen partial pressure of from 5 to 1000, preferably from 20 to 500, in particular from 50 to 200, bar.

Preferred hydrogenation catalysts are metals of group VIII of the periodic table, in particular nickel or cobalt catalysts, as well as noble metal catalysts such as palladium, platinum or rhodium. The catalyst metals can be used in the form of solid catalysts, for example in finely divided form, such as Raney nickel or Raney cobalt, in suspension or in a magnetically fixed form, as mixed catalysts or as a deposit on a carrier. Examples of suitable carriers are alumina, silica gel and magnesium silicates.

The catalytically active metals are particularly advantageously used in finely divided form, and skeleton catalysts have therefore proven particularly useful.

Particularly preferred catalysts are those which are prepared by calcining compounds of the formula I

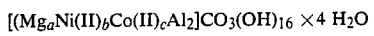

where a is an integer or decimal number from 0 to 4 and b and c are each an integer or a decimal number from 0 to 6, with the proviso that $2(a+b+c)=12$, at from 200° to 600° C. and then reducing the product with hydrogen at elevated temperatures, for example from 350° to 400° C.. Catalysts which have proven particularly useful are those obtained by calcining and reducing compounds of the following formulae:

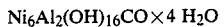

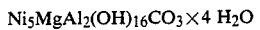

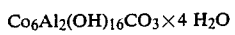

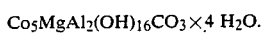

The compounds of the formula I are obtained, for example, as follows: nickel, aluminum, cobalt and magnesium, in the form of their water-soluble salts, eg. chlorides, sulfates or, preferably, nitrates, are dissolved together in water, in a ratio which corresponds very closely to the desired composition of the catalyst and conforms in its stoichiometry to the formula I.

The overall molarity of the metal salt solution should be from 0.5 to 3, preferably from 1.0 to 2, with respect to metal ions. The metal salt solution is heated to 50°–100° C., preferably 100° C., and, in the course of from 0.5 to 10, preferably 3, minutes, combined with an equivalent amount or, preferably, a slight excess of a 1–3, preferably 1.5–2.5, molar solution of an alkali metal bicarbonate which has been heated to 50°–100° C., preferably 80°–100° C. Advantageously, the alkali metal bicarbonate is used in an excess of up to 20, preferably from 0.5 to 3, % by weight, based on the theoretical amount of bicarbonate. After the addition of the metal salt solution, stirring is advantageously carried out for a further 10–30, preferably 15–25, minutes, after which the resulting precipitate is filtered off, washed with water and dried at from 50° to 200° C., preferably from 100° to 160° C.. The basic carbonates are obtained in virtually quantitative yields. Particularly suitable alkali metal bicarbonates are sodium bicarbonate and potassium bicarbonate. However, it is also possible to use ammonium bicarbonate for the precipitation. Of course, mixtures of the stated bicarbonates may also be employed. It is also possible to carry out the precipitation of the metal ions using solutions of alkali metal carbonates, such as sodium carbonate and/or potassium carbonate, if carbon dioxide is passed into the initially taken alkali metal carbonate solution during precipitation; however, in the long run this amounts to precipitation with bicarbonate. Calcination is advantageously carried out at from 250° to 400° C. for a period of, for example, from 5 to 40, in particular from 15 to 30, hours. Before the catalyst is actually used, it is advantageously reduced with hydrogen at from 180° to 500° C., preferably from 250° to 450° C., in the course of from 5 to 100, advantageously from 10 to 100, hours.

Other preferred catalysts are nickel catalysts which contain nickel in finely divided form applied on a carrier, in particular magnesium silicate. Such catalysts advantageously contain from 30 to 60% by weight, based on the total catalyst material including the carrier. Catalysts of this type are described in, for example, German Patent No. 1,545,428.

Raney nickel or Raney cobalt is preferably used as the catalyst, a suspension procedure being employed or the catalyst being fixed in the reaction zone on permanent magnets or on soft iron elements in a magnetic or electromagnetic field. Such magnets are arranged, for example, in the form of rods in the reaction zone.

It has furthermore proven advantageous for the reaction if a residence time of from 1 to 30 minutes and a space velocity of 0.2 to 2.0 kg of 5-formylvalerate per liter of catalyst per hour are maintained.

The reaction can be carried out batchwise, for example in a high pressure vessel, but is preferably carried out continuously, for example in pressure-tight stirred containers, eg. a stirred cascade. It has proven advantageous to avoid back-mixing during the reaction. For this reason, tube reactors have proven particularly useful; in these reactors, the alcoholic solution of the 5-formylvalerate and ammonia are passed over a fixed-bed catalyst. The liquid phase method has proven particularly suitable here.

Mixtures of 6-aminocarboxylates, the alkanol present, excess ammonia and minor amounts of s-caprolactam are obtained as the reacted mixture from stage a after the let-down step, during which the hydrogen is removed.

Where methyl 5-formylvalerate is used and methanol is employed as the solvent, a reaction mixture consisting of methyl 6-aminocaproate in methanol and containing from 1 to 10 mol %, based on methyl 6-aminocaproate, of caprolactam, as well as ammonia, is obtained.

In a second stage b, the excess ammonia and dissolved hydrogen are removed from the reaction mixture. This is effected, for example, by distillation or by stripping with an inert gas. The ammonia and excess hydrogen obtained are advantageously recycled to stage a. It has proven particularly advantageous if an ammonia content of from 0.1 to 2, in particular from 0.1 to 1, % by weight is maintained in the solution to be used further.

The resulting reaction mixture, which essentially contains 6-aminocaproic acid, alkanols and small amounts of ammonia and ε-caprolactam, is then reacted with water, with simultaneous removal of the alkanol, at elevated temperatures (step c).

The weight of water used is preferably from 1 to 20, in particular from 3 to 10, times the total content of 6-aminocaproate and ε-caprolactam.

The reaction temperature is advantageously from 50° to 250° C., in particular from 80° to 150° C. Depending on the reaction temperature, the reaction is carried out under atmospheric or superatmospheric pressure, for example up to 5 bar, batchwise or continuously. The procedure is preferably carried out continuously, for example in stirred reactors or stirred reactor cascades, which are equipped with suitable distillation means for separating off the alkanol.

The alkanols removed are advantageously recycled to the hydrogenation stage (a).

Conversions of 6-aminocaproate of ≧90%, in particular ≧95%, are advantageous.

It has also proven useful to combine stages c and d and initially to distil off ammonia in a column, and to carry out the reaction in the presence of water or simultaneously distilling off alkanols. In this procedure, the reaction mixture from stage a, after being let down, is advantageously fed to the middle part of the column, and water is fed to the bottom qf the column. Ammonia and alkanols are distilled off, while an aqueous solution of 6-aminocaproic acid is obtained as the bottom product.

In (d), 6-aminocaproic acid, which is obtained as the reacted mixture from the preceding hydrolysis stage (c), is subjected to cyclocondensation to give caprolactam.

The reacted mixture from stage c is preferably used directly. If necessary, however, the reacted mixture may be concentrated, for example by distilling off some of the water, or diluted by adding water.

The cyclocondensation is preferably carried out using solutions which contain from 1 to 20, in particular from 2 to 10, % by weight of 6-aminocaproin acid. The reaction is effected at from 150° to 370° C., in particular from 250° to 330° C., in general under the autogenous pressure of the reaction mixture or under superatmospheric pressure, batchwise or continuously, for example in a tube reactor. The mean residence times for the reaction are from 0.1 to 2 hours.

The caprolactam formed is isolated by distillation or, preferably, extraction, for example using an extracting agent such as methylene chloride, chloroform, cyclohexane or trichloroethylene.

EXAMPLE

Stage (a)

A vertical tube reactor having a diameter of 16 mm and a load height of 25 cm and possessing an oil-heated double jacket was charged with 50 ml of a nickel catalyst containing 55% by weight of finely divided nickel oxide on magnesium silicate, in the form of extrudates of 1.5 mm diameter. The catalyst was reduced in the course of 18 hours while increasing the temperature stepwise from 60° to 330° C. and raising the hydrogen content in the nitrogen-hydrogen mixture used for the reduction from 5 to 50%.

Thereafter, 198.9 g/hour of a 10.0% strength methanolic methyl 5-formylvalerate solution and 36.5 g/hour of liquid ammonia were pumped through the reactor while simultaneously passing through hydrogen at 80° C. and under 100 bar. The reaction mixture passed from the top of the reactor via a condenser to a separator, from which the reaction mixture and 26.2 l/hour of waste gas were removed.

According to analysis by gas chromatography, the reaction mixture contained 7.2% by weight of methyl 6-amino-caproate and 0.12 % by weight of ε-caprolactam.

Stages (b) and (c):

In a stirred flask on which an 80 cm high packed column containing V₂A stainless steel wire mesh rings of 5 mm diameter was mounted, 500 g of water were heated at the boil (100° C.). The reacted mixture from stage a was passed into the middle of the column in the course of 6 hours, and ammonia, methanol and a little water were separated off via the top (boiling point limit 65° C.). In addition, 995 g of water were pumped continuously into the flask during the final 4 hours, and at the same time the height of the charge was kept constant by pumping off reaction mixture using a second pump. When the experiments were terminated, a total of 1540.2 g of reaction mixture (hydrolysis product) were obtained (solution pumped off, including solution present in the bottom of the column).

Stage (d)

The solution obtained from the preceding stage was then pumped continuously in the course of 11 hours under 110 bar through a tube reactor (coiled tube) which had a length of 8.71 m and a diameter of 3.17 mm and was kept at 330° C. by means of an oil thermostat. At the outlet of the tube reactor, the reaction mixture was cooled to room temperature and let down to atmospheric pressure. Thereafter, the reactor was flushed for one hour by pumping through water. A total of 1661.1 g of mixture was discharged. According to quantitative analysis by high pressure liquid chromatography, this mixture contained 4.6% by weight of ε-caprolactam and 0.18% by weight of 6-aminocaproic acid, corresponding to a yield of 81.6% of ε-caprolactam and 2.8% of 6-aminocaproic acid, the percentages being based on the methyl 5formylvalerate used in stage a.

EXAMPLE 2

The procedure described in Example 1 was followed, except that stage a was carried out as follows:

In a vertical tube reactor having a diameter of 14 mm and a length of 450 mm, a rod of 9 mm diameter was arranged concentrically, and permanent magnets (having a field strength of 500 Gauss) were attached to the said rod. The magnets were laden only with 11.0 g of Raney nickel, this being done by passing a suspension of Raney nickel and water through the reactor from below.

Thereafter, 77.3 g/hour of a 12.0% strength by weight methanolic methyl 5-formylvalerate solution and 24 ml/hour of liquid ammonia were pumped through the reactor from below while simultaneously passing through 8.7 of hydrogen at 76° C. and under 80 bar. The reaction mixture passes from the top of the reactor via a pressure relief valve to stage 3.

Stages (b), (c) and (d) were carried out as described in Example 1. The resulting yield of caprolactam was 85%.

We claim

1. A process for the preparation of ε-caprolactam, wherein
   (a) a $C_1$-$C_4$-alkyl 5-formylvalerate is reacted with excess ammonia and hydrogen in the presence of an alkanol as the solvent and in the presence of a hydrogenation catalyst under superatmospheric pressure in the liquid phase at from 40 to 130° C.,
   (b) exesss ammonia and hydrogen are separated off from the reaction mixture,
   (c) the resulting reaction mixture is reacted with water at elevated temperatures with simultaneous removal of alkanols, and
   (d) the reaction mixture thus obtained is heated to 150°–370° C. and ε-caprolactam is obtained.

2. The process of in claim 1, wherein the catalyst used is obtained by calcining a compound of the formula I

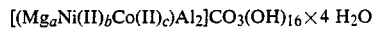

$$[(Mg_a Ni(II)_b Co(II)_c)Al_2]CO_3(OH)_{16} \times 4\ H_2O$$

where a is an integer or decimal number from 0 to 4 and b and c are each an integer or a decimal number from 0 to 6, with the proviso that 2 (a+b+c)=12, at from 200° to 600° C. and then reducing the product with hydrogen at elevated temperatures.

3. The process of claim 1, wherein a nickel catalyst which contains from 30 to 60% by weight of finely divided nickel deposited on magnesium silicate is used.

4. The process of claim 1, wherein a $C_1$-$C_4$-alkyl 5-formylvalerate in solution with the alkanol and ammonia is passed over a fixed-bed catalyst by the liquid phase method.

5. The process of claim 1, wherein Raney nickel or Raney cobalt is used in suspension.

6. The process of claim 1, wherein Raney nickel or Raney cobalt is fixed magnetically or electromagnetically in the reaction zone.

7. The process of claim 1, wherein a residence time of from 1 to 30 minutes is maintained in stage a.

8. The process of claim 1, wherein a space velocity of from 0.2 to 2.0 kg of the $C_1$-$C_4$-5-formylvalerate per liter of catalyst per hour is maintained.

9. The process of claim 1, wherein methyl 5-formylvalerate dissolved in methanol is used.

10. The process of claim 1, wherein the reaction is carried out at from 80 to 150° C. in stage (c).

* * * * *